US00PP25767P3

(12) United States Plant Patent
Skogerboe

(10) Patent No.: US PP25,767 P3
(45) Date of Patent: Aug. 4, 2015

(54) CHOKECHERRY TREE NAMED 'P002S'

(50) Latin Name: ***Prunus* spp.**
Varietal Denomination: P002S

(71) Applicant: Plant Select, Fort Collins, CO (US)

(72) Inventor: Scott Thomas Skogerboe, Fort Collins, CO (US)

(73) Assignee: Plant Select, Fort Collins, CO (US)

( * ) Notice: Subject to any disclaimer, the term of this patent is extended or adjusted under 35 U.S.C. 154(b) by 277 days.

(21) Appl. No.: 13/694,370

(22) Filed: Nov. 26, 2012

(65) Prior Publication Data

US 2014/0150144 P1 May 29, 2014

(51) Int. Cl.
*A01H 5/00* (2006.01)
*A01H 5/08* (2006.01)

(52) U.S. Cl.
USPC ..... Plt./216
CPC ..... *A01H 5/085* (2013.01)

(58) Field of Classification Search
USPC ..... Plt./216, 226
CPC ..... A01H 5/00; A01H 5/02; A01H 5/0837; A01H 5/0831
See application file for complete search history.

*Primary Examiner* — June Hwu

(57) ABSTRACT

A new and distinct variety of *Prunus* spp. chokecherry tree named 'P002S' that is characterized by the complete absence of suckering; strong upright, uniformly broad and oval, single trunk tree form; vibrant and glossy leaves that emerge green and mature into dark reddish-purple foliage; and strong hybrid vigor.

3 Drawing Sheets

Latin name of the genus and species of the plant claimed: The chokecherry variety of this invention is botanically identified as *Prunus* spp.

Variety denomination: The variety denomination is 'P002S'.

BACKGROUND OF THE INVENTION

The present invention relates to a new and distinct tree variety of *Prunus* spp. more commonly known as chokecherry, which can be grown for use as a single trunk, ornamental shade tree.

Chokecherry plants are well known in the industry for their shrub-like appearance and for dominant root suckering leading to invasive growth habit. This growth habit has limited the use of chokecherry in the industry as an ornamental plant despite the other preferred characteristics of chokecherry plants, namely attractive burgundy foliage, thickets of branches for privacy and for wildlife habitat. The present invention, in contrast, meets the needs of providing qualities of a preferred ornamental chokecherry plant with the distinction of the complete absence of suckering; strong upright, uniformly broad and oval single trunk tree form; large, vibrant and glossy leaves that emerge green and mature into dark reddish-purple foliage; and strong hybrid vigor.

The present invention is a product of a discovery and selection in a cultivated seed orchard located in Helena, Mont. in July 1998 and subsequent propagation of the softwood cuttings from discovered plant by the inventor. The surrounding plants where the invention was found demonstrated characteristics typical of chokecherry plants in demonstration of prevalent suckering characteristics and multi-stem growth habit typical of the red leaf form of *Prunus virginiana*, which is in contrast to the discovered present invention.

While parentage of the present invention is unknown, the surrounding plants located nearby where the present invention was discovered may be the result of a conventional hybridization between the neighboring cultivated plants of the red leafed forms of *Prunus virginiana* and possibly *Prunus padus*. *Prunus virginiana* provides the distinctive red leaf coloration; therefore its contribution in the parentage of the claimed plant is considered probable. Patent status of the plants in the cultivated area is unknown.

Since the lineage of the present invention is unknown, comparison with known commercial varieties is drawn generally to the commercially available, related plant species. 'P002S' differs primarily from red leafed forms of *Prunus virginiana* plants by demonstrating the complete absence of root suckering as well as a strong upright, uniformly broad and oval, single trunk tree form; whereas *Prunus virginiana* exhibit extensive root suckering and multi-stem branching. Furthermore, 'P002S' is distinct from *Prunus padus* through the demonstration of non-typical smooth, glossy leaves that emerge green and mature into reddish-purple, and hybrid vigor.

The inventor selected and transported softwood cuttings of the discovered plant in July 1998 to another cultivated area in Fort Collins, Colo. where the present invention was observed for 10 years before beginning asexual propagation through vegetative cuttings in the spring of 2008.

The present invention has been asexually propagated in a controlled nursery environment for five generations through vegetative cuttings under the direction of the inventor. The generations of the new variety, 'P002S', have demonstrated that the combination of characteristics disclosed are stable and firmly fixed and are retained true to type through successive generations of asexual reproduction. Additional testing has been conducted in nurseries in Minnesota (St. Paul) and Oregon (both Boring and Dayton), all beginning in 2009. Observations and characteristic data disclosed herein were collected in the summer of 2012 in Fort Collins, Colo.

Plant Breeder's Rights for this variety have not been applied for and 'P002S' has not been made publicly available or sold more than a year before the filing date of this application.

BRIEF SUMMARY OF THE INVENTION

The following traits have been repeatedly observed and represent the characteristics of the new Chokecherry tree variety 'P002S'. These traits in combination distinguish this variety from all other commercial varieties known to the inventor.

1. Complete absence of root suckering;
2. Strong upright, uniformly broad and oval, single trunk tree form;
3. Large, vibrant and glossy leaves that emerge green and mature into dark reddish-purple foliage; and
4. Strong hybrid vigor.

Plants of the present invention have not been observed under all possible environmental and cultural conditions. The phenotype may vary somewhat with variations in environmental conditions, for example, with fluctuation in temperature and light intensity without, however, any variance in genotype.

BRIEF DESCRIPTION OF THE PHOTOGRAPH(S)

The accompanying colored photographs illustrate the overall appearance of the new and distinct Chokecherry tree showing the colors as true as it is reasonably possible to obtain in colored reproductions of conventional photography. Colors in the photograph may differ slightly from the color values cited in the detailed botanical description which accurately describe the colors of the new Chokecherry tree.

FIGS. 1 through 5 were taken in the summer of 2012 of the present invention, a tree approximately 13 years of age, in a nursery in Fort Collins, Colo., grown under conditions which approximate those generally used in commercial practice.

FIG. 1 demonstrates distinguishing characteristics of the present invention with the complete absence of root suckering; strong upright, uniformly broad and oval, single trunk tree form, and the reddish-purple foliage of late summer.

FIG. 2 demonstrates the point in time when most of the foliage has turned purple yet the tips remain green, as well the complete absence of root suckering.

FIG. 3 demonstrates the tree in spring, with full bloom, green stage foliage and the complete absence of root suckering.

DETAILED BOTANICAL DESCRIPTION OF THE PLANT

Figure 1:
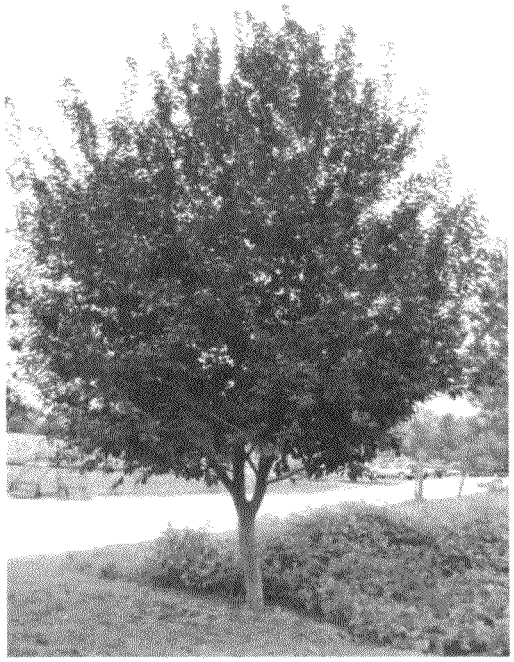
Figure 2:
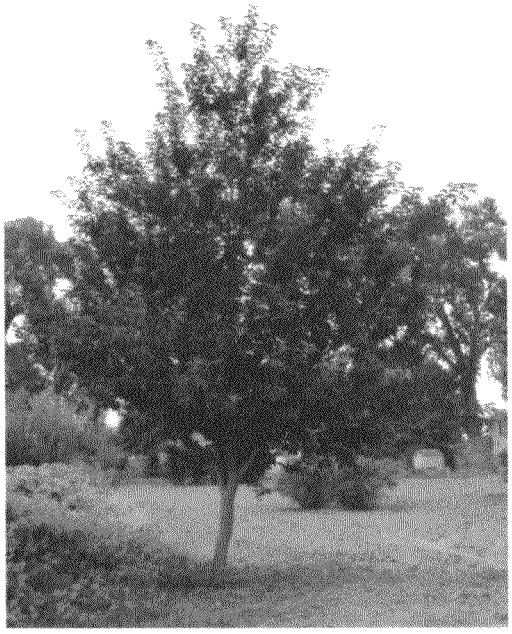
Figure 3:
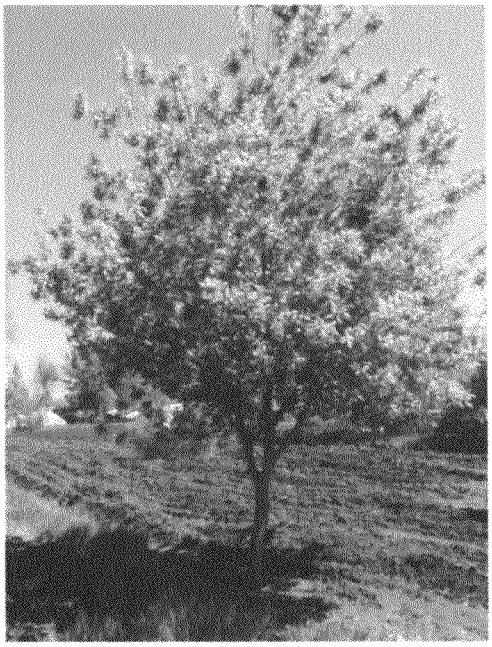
Figure 4:
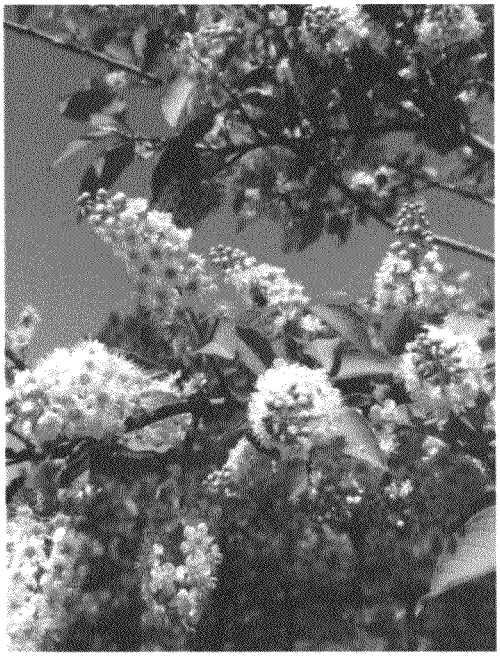
FIG. 4 shows a close-up of the flowers.
Figure 5:
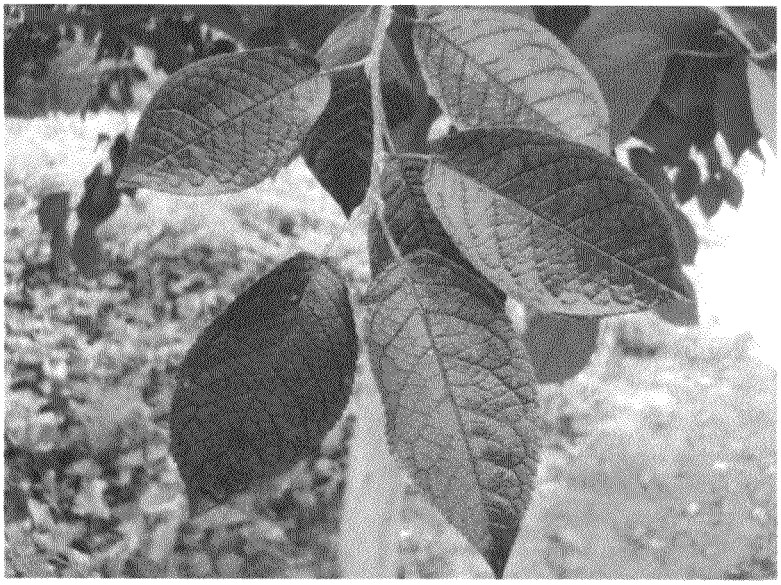
FIG. 5 shows a close-up of the large, vibrant and glossy leaves in the dark reddish-purple stage.

The following is a detailed description of the new variety 'P002S'. Data was collected from a tree approximately 13 years old, presently growing outdoors in a nursery in Fort Collins, Colo. The growing conditions approximate those generally used in commercial practice. The color determinations are in accordance with the 2005 edition of The Royal Horticultural Society Mini Colour Chart published by The Royal Horticultural Society (London, England), except where general color terms of ordinary dictionary significance are used and color readings were observed under natural, outdoor light.

Classification:

*Family.*—Rosaceae.

*Botanical.*—*Prunus* spp.

*Common.*—Chokecherry.

Parentage: Unknown.

Propagation: Vegetative cuttings.

Tree:

*Ploidy.*—Diploid.

*Tree height, unpruned* (*m*).—7.92 m.

*Tree vigor.*—Moderately vigorous.

*Tree shape.*—Upright, oval.

*Growth habit.*—Upright, oval.

*Canopy width* (*m*).—6.00 m.

*Canopy height* (*m*).—6.40 m.

*Canopy volume, swag* ($m^3$).—475.00 $m^3$.

*Canopy shape.*—Upright, broad and oval.

Trunk and branches:

*Trunk texture.*—Smooth.

*Trunk diameter* (*cm*).—17.5 cm taken at 30.48 cm above the ground.

*Trunk bark color.*—RHS Grey Group 201 C.

*Branch length* (*m*).—3.50 m from trunk to branch tip.

*Branch texture.*—Smooth.

*Branch color.*—RHS Grey Group 201 B.

*Branch arrangement.*—Alternate.

*Crotch angle from main trunk.*—Strong, greater than 60°.

Leaves:

*Size* (*lamina average*).—a. Length (mm): 98.0 mm. b. Width (mm): 55.0 mm.

*Type.*—Simple.

*Shape.*—Broad elliptic.

*Apex.*—Acuminate.

*Base.*—Broad cuneate to rounded.

*Margin.*—Serrulate.

*Cross section.*—Concave.

*Leaf blade length* (*mm*).—98.0 mm.

*Leaf blade width* (*mm*).—55.0 mm.

*Leaf coloration at emergence.*—a. Upper surface color: RHS Green Group 141D. b. Lower surface color: RHS Green Group 138D.

*Fall foliage coloration.*—RHS 183A (purple brown).

*Surface.*—a. Upper surface texture: Glabrous. b. Lower surface texture: Glaucous with reticulate venation. a. Upper surface color: RHS Brown Group 200 A. b. Lower surface color: RHS Brown Group 200 A.

*Venation.*—Reticulate.

*Petiole.*—a. Shape: Long glandular. b. Length (mm): 21.0 mm. c. Width (mm): 2.0 mm. d. Color: RHS Greyed Red Group 178 A. e. Thorns, Spines: Absent.

Flowers:

*Inflorescence type.*—Raceme.

*Average inflorescence size.*—a. Diameter (mm): 65.0 mm. b. Length (mm): 200.0 mm.

*Age of tree of first bloom.*—5 year from rooted cutting.

*Bloom habit.*—Once annually in spring.

*Time of year for first bloom.*—Late April to early May.

*Length of blooming time* (*days*).—7 to 10 days for petal drop.

*Structure.*—Complete.

*Average size.*—a. Length (mm): 8.0 to 9.0 mm. b. Width (mm): 12.0 mm.

*Arrangement.*—Typical.

*Fragrance.*—Sweetly fragrant.

*Peduncle.*—a. Average length (mm): 190.0 mm. b. Surface texture: Smooth. c. Color: RHS 141D.

*Bud.*—a. Shape: Narrowly conical. b. Length (mm): 5.0 to 7.0 mm. c. Width (mm): 2.0 to 3.0 mm. d. Color: RHS Brown Group 200 D.

*Petal.*—Number, average: 5. Length (mm): 3.0 to 4.0 mm. Width (mm): 3.0 to 4.0 mm. Shape: Irregular, rounded. Apex shape: Irregular, obcordate. Base shape: Acute. Margin: Crinkled. Color: a. Upper Surface: RHS White Group 155 D. b. Lower Surface: RHS White Group 155 D.

*Sepals.*—Number (per flower): 5. Shape: Acute. Surface texture: Smooth. Color: RHS 141D. Length (mm): 1.0 to 1.5 mm. Width (mm): 1.5 to 2.0 mm. Apex: Acute. Margin: Smooth.

*Pedicel.*—Surface texture: Smooth. Length (mm): 10.0 to 15.0 mm. Width (mm): 1.0 mm. Color: RHS Greyed-Yellow Group 160 B.

*Calyx.*—Present.

Reproductive organs:

*Fertility.*—Self-fertile.

*Stamen.*—a. Number: 20 to 22. b. Length (mm): 2.0 to 3.0 mm. c. Color: RHS White Group 155 D.

*Anther.*—a. Length (mm): Less than 1.0 mm. b. Width (mm): Less than 1.0 mm. c. Color: RHS Yellow Group 12 D. d. Filament length (mm): 1.0 to 3.0 mm.

*Pistil.*—a. Number: 1. b. Length (mm): 2.0 mm. c. Color: RHS Greyed-Yellow Group 162 C.

*Style.*—a. Length (mm): 1.0 mm. b. Width (mm): Less than 1.0 mm. c. Color: RHS Greyed-Yellow Group 160 B.

*Ovary.*—a. Shape: Ovate. b. Diameter (mm): 1.0 mm. c. Color: RHS Greyed-Yellow Group 160 A.

*Pollen color.*—RHS Yellow Group 12 D.

Fruit:

*Time of season when first appears.*—Early July.

*Size.*—a. Length (mm): 5.0 to 6.0 mm. b. Width (mm): 4.0 to 5.0 mm.

*Shape.*—Ovoid.

*Color.*—RHS Black Group 202 A.

Best mode growing conditions:

*Soil conditions.*—Highly adaptable to various non-compacted soil types.

*Water use/drought tolerance.*—Moderately xeric while performing best with bi-monthly deep irrigation.

*Fertilization.*—a. Propagation: None required but a starter solution of 100 ppm Nitrogen is beneficial during misting. b. Maintenance: Once rooted 100 ppm Nitrogen from a balanced water soluble blend of NPK with each irrigation during the growing season.

Insects and disease: Susceptible to Tent Caterpillar, Black Knot.

I claim:

1. A new and distinct variety of chokecherry tree having the characteristics substantially as described and illustrated herein.

* * * * *